United States Patent

DiGiacomo et al.

[19]

[11] Patent Number: 6,116,772
[45] Date of Patent: Sep. 12, 2000

[54] DISPOSABLE BOWL AND SPATULA

[75] Inventors: Ellen V. DiGiacomo; James R. DiGiacomo, both of Littleton; Christopher R. Johnson; Rita J. Johnson, both of Concord, all of Mass.

[73] Assignee: Millennium Advantage Products, Littleton, Mass.

[21] Appl. No.: 09/175,069

[22] Filed: Oct. 19, 1998

Related U.S. Application Data

[63] Continuation-in-part of application No. 09/089,432, Jun. 3, 1998.

[51] Int. Cl.[7] .................................................. A61C 5/06
[52] U.S. Cl. ............................ 366/130; 366/602; 73/427
[58] Field of Search .................................. 366/602, 130, 366/349; 15/236.06, 236.01; 220/674, 675, 657, 659; 206/220, 219, 553, 368, 369, 370, 372; D7/543, 318; D24/221; 30/324, 325; D10/46.2; 73/426, 427

[56] References Cited

U.S. PATENT DOCUMENTS

| 153,159 | 7/1874 | Dinwiddie | 73/427 |
|---|---|---|---|
| D. 208,319 | 8/1967 | Manseau | D7/515 |
| D. 222,177 | 10/1971 | Tonyer | D7/543 |
| D. 250,565 | 12/1978 | Stowell | D7/543 |
| D. 304,537 | 11/1989 | McCarroll | D10/46.2 |
| D. 404,663 | 1/1999 | Prindle | D10/46.2 |
| 476,136 | 5/1892 | Eustis | 73/427 |
| 641,052 | 1/1900 | Strauss | 73/427 |
| 2,195,133 | 3/1940 | Nevin | 15/236.01 |
| 2,758,771 | 8/1956 | Bauer | 73/427 |
| 2,803,375 | 8/1957 | Meshbert | 206/515 |
| 2,860,858 | 11/1958 | Kurs | 366/129 |
| 3,411,723 | 11/1968 | Kohn | 15/236.01 |
| 3,710,589 | 1/1973 | Brown et al. | 62/371 |
| 3,933,246 | 1/1976 | Fulton | 220/70 |
| 4,008,803 | 2/1977 | Smith | 206/220 |
| 4,079,629 | 3/1978 | Hope | 73/427 |
| 5,100,241 | 3/1992 | Chan | 366/139 |

FOREIGN PATENT DOCUMENTS

| 986 100 | 7/1951 | France | 15/236.01 |
|---|---|---|---|
| 37 24 007 | 2/1989 | Germany | 15/236.01 |

*Primary Examiner*—Tony G. Soohoo
*Attorney, Agent, or Firm*—George A. Herbster; Pearson & Pearson

[57] ABSTRACT

A kit for facilitating the mixing of ingredients in a medical office. The kit includes at least one free-standing, disposable bowl and one dual-purpose disposable spatula. Each free-standing, disposable bowl has a closed bottom for supporting the bowl in an upstanding position. An integrally molded, radially, outwardly extending planar lip around the periphery of the top imparts rigidity to the bowl. The free-standing disposable bowl can then be used for mixing ingredients without the requirement for any additional support structure. The dual-purpose spatula has one shape that conforms to the bowl for optimizing the mixing of one set of ingredients and another shape at the other end thereof for optimizing the mixing of other ingredients.

19 Claims, 7 Drawing Sheets

DISPOSABLE BOWL AND SPATULA

CROSS REFERENCE TO RELATED APPLICATION

This is a continuation-in-part of copending application Ser. No. 09/089,432 filed Jun. 3, 1998 entitled Disposable Bowl and Spatula which application is assigned to the same assignee as this invention.

BACKGROUND OF THE INVENTION

1. Field of the Invention

This invention generally relates to implements for mixing ingredients used in medical offices and particularly in dental offices.

2. Description of Related Art

Procedures formed in medical offices, oftentimes require individuals to combine ingredients in mixtures. In dental offices, for example, personnel commonly mix alginate for making impressions or mix gypsum (i.e., a mixture of water with either plaster or stone) for making positive casts used for fabricating bleaching trays, night guards, diagnostic study models, temporary crowns and the like.

Historically, individuals mix ingredients in a reusable rubber mixing bowl and with a reusable spatula. Rubber bowls and spatulas harbor many disease producing microbes, such as hepatitis B, that without proper precautions can transfer from one patient to another. To avoid cross contamination by such microbes it is necessary to sterilize these items by a complex disinfecting procedure. In accordance with such disinfecting procedures, each implement is washed in warm, soapy water, rinsed and dried. Then an individual sprays the implement with an appropriate disinfectant and allows the implement to air dry for 10 minutes or so before storing the implement for future use. When the implement is to be used again, it must be rinsed under running water to remove any residual disinfectant and then dried. As will be apparent, personnel time makes this an inefficient and expensive process.

A number of approaches have been proposed for simplifying this process and making it less cumbersome by providing disposable means for mixing. One alternative in widespread use comprises a rigid heavy rubber bowl support with a common plastic disposable bowl liner wherein the liner relies upon the bowl support for rigidity during mixing. While the bowl liner is a disposable item, the bowl support is not. Consequently after each use it is necessary to disinfect the bowl support with the same process as previously described. It has been observed that in many situations individuals, for reasons of forgetfulness or lack of time, overlook the requirement for disinfecting the support and merely put it away apparently and erroneously relying upon disposal of the bowl liner as eliminating any possible cross contamination. As will be apparent, this is not a valid assumption. That is, microbes will transfer to the bowl support during use, so these microbes can populate and survive on the bowl support if disinfectant is not applied. Consequently, even with the disposable bowl liner, the above-mentioned disinfecting procedure still is required.

The process for mixing ingredients in bowls and the process for washing and disinfecting reusable bowls, reusable spatulas and bowl supports involve significant repetitive hand-wrist motions that can aggravate symptoms of carpal tunnel syndrome and tendinitis. Moreover, it is often desirable to eliminate any air entrained in a final mixture. Reusable bowls can be used with vibrators to mix gypsum and displace air from the mixture. The elimination of air from a mixture in a bowl liner is less efficient than a reusable bowl because the two-part nature of the bowl support and bowl liner tends to dampen any vibrations that reach the mixture.

As another example, U.S. Pat. No. 5,106,297 to Discko discloses a dental tray used in the preparation of single or multiple component bonding liquids and sealants. The tray has multiple depressions configured to hold a bottle having a cap with the shoulder upside down. This allows a dentist to dispense single or multiple component bonding liquids and sealants. Distinctively shaped wells avoid confusion as to the function of each well. A finger indentation in the side opposite the depressions facilitates holding the tray during lightweight mixing or use.

U.S. Pat. No. 5,240,415 to Haynie discloses a dental bleach system that has separate compartments for fumed silica and for hydrogen peroxide. The fumed silica is provided in a predetermined quantity in a mixing chamber while the hydrogen peroxide is provided as a pre-measured volume in an ampule. The system also includes a spatula for enabling the mixing of the materials in the compartment holding the fumed silica. The package is completed with a sealing cover.

U.S. Pat. No. 5,465,833 to Tarter discloses a dental impression material package. The package includes a bag that encloses dental impression powder and a valve that extends through the bag. Water can be injected through the valve by means of a syringe. After mixing materials within the bag, air can be removed by means of a syringe inserted through the valve. In one embodiment alginate is extruded from the bag through the valve into an impression tray.

Other examples of products adapted for mixing materials for dental or eye care include U.S. Pat. No. 4,852,742 to Scuorzio and U.S. Pat. No. 5,456,361 to Walsh et al. The Scuorzio patent discloses a kit assembly for oral hygiene care. A first compartment contains baking soda; a second compartment receives hydrogen peroxide. The baking soda compartment serves as a repository for the mixture and a receptacle for receiving a toothbrush. The Walsh et al. patent discloses a tray with receptacles for hygienic care items and includes receptacles for rinsing contact lenses and for receiving used mouthwash.

The foregoing examples of devices for mixing ingredients are oftentimes large. Moreover, their mixing volumes are not sufficient for many of the mixtures required in medical offices.

As particularly shown in the Discko and Haynie patents, the kits in the prior art usually include a spatula. These could benefit from being disposable in the same way as the mixing bowls. However, the shape of a spatula impacts the efficiency with which ingredients mix and the optimal shape may vary from one mixture to another. The inventory of prior art disposable spatulas required stocking differently shaped spatulas. However, oftentimes personnel in a medical office elect to stock only a few reusable spatulas of each type even though it becomes necessary to disinfect these spatulas after each use.

None of the prior art discloses or suggests a mixing system in which the components are completely disposable. There remains a need for a one-piece, free-standing, disposable bowl adapted for mixing various materials and disposable spatulas for optimizing the mixing process.

SUMMARY

Therefore it is an object of this invention to provide a free-standing, disposable bowl for mixing ingredients in a medical environment, particularly a dental environment.

Another object of this invention is to provide a free-standing, disposable bowl for mixing ingredients that has a minimal cost.

Still another object of this invention is to provide a free-standing, disposable bowl with sufficient rigidity to eliminate any need for an external support element during the mixing of ingredients.

Yet another object of this invention is to provide a free-standing, disposable bowl and spatula for optimizing mixing within the bowl.

Yet still another object of this invention is to provide a kit comprising a plurality of mixing bowls and spatulas that are adapted for combining ingredients into different mixtures in an optimal manner.

Still yet another object of this invention is to provide a fully disposable mixing bowl and spatula that eliminate cleanup operations.

Another object of this invention is to provide a fully disposable mixing bowl and spatula that reduce aggravation of carpal tunnel syndrome, tendinitis and like medical problems.

In accordance with one aspect of this invention a free-standing disposable bowl for mixing ingredients comprises an integrally molded, plastic bowl having a closed bottom and an open top. The closed bottom is smaller than the open top and provides a planar support for the bowl. The bowl additionally includes an outwardly extending, planar lip at the open top for imparting rigidity to the bowl.

In accordance with another object of this invention a system for facilitating the mixing of ingredients in a dental facility includes a free-standing, disposable bowl for mixing ingredients and a disposable spatula for mixing the ingredients in the disposable bowl. The disposable bowl includes an integrally molded plastic bowl having a closed, flat bottom and open top. The closed bottom is smaller than the open top and provides support for the bowl in an upstanding orientation. The bowl additionally includes an integrally molded, outwardly extending planar lip for imparting rigidity to the bowl.

In another embodiment of this invention a kit for enabling the mixing of materials in a dental facility includes a first plurality of nested free-standing disposable bowls, a second plurality of disposable spatulas and packaging for containing the plurality of bowls and spatulas. In this kit each bowl comprises a plastic bowl having a closed bottom and open top that is integrally molded from an a FDA approved, high impact polystyrene material. The closed bottom is smaller than the open top and is flat to provide planar support for the bowl in an upstanding orientation. The bowl additionally includes an integrally molded, radially outwardly extending continuous circumferential planar lip about the open top for imparting rigidity to the bowl.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
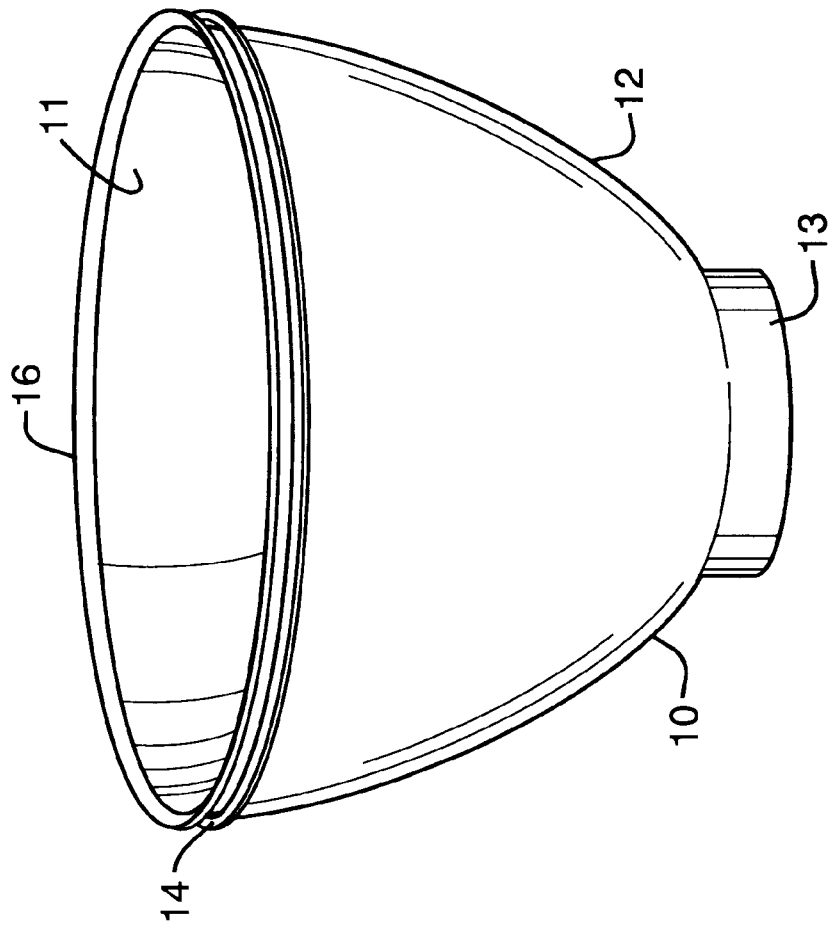
FIGS. 1 and 2 are perspective views that depict a prior art reusable rubber bowl support and bowl liner.

As previously indicated one of the popular mixing bowl implementations includes a bowl support and bowl liner. In the particular embodiment shown in FIGS. 1 and 2 a rubber bowl support 10 carries a bowl liner 11. The bowl support 10 has a bowl-shaped body 12, a cylindrical base 13 and thick walls that terminate at a plane open top 14. The bowl support 10 is usually composed of a hard rubber material. Its thickness is selected so that it provides necessary rigidity during the mixing of the materials in the liner.

Figure 2:
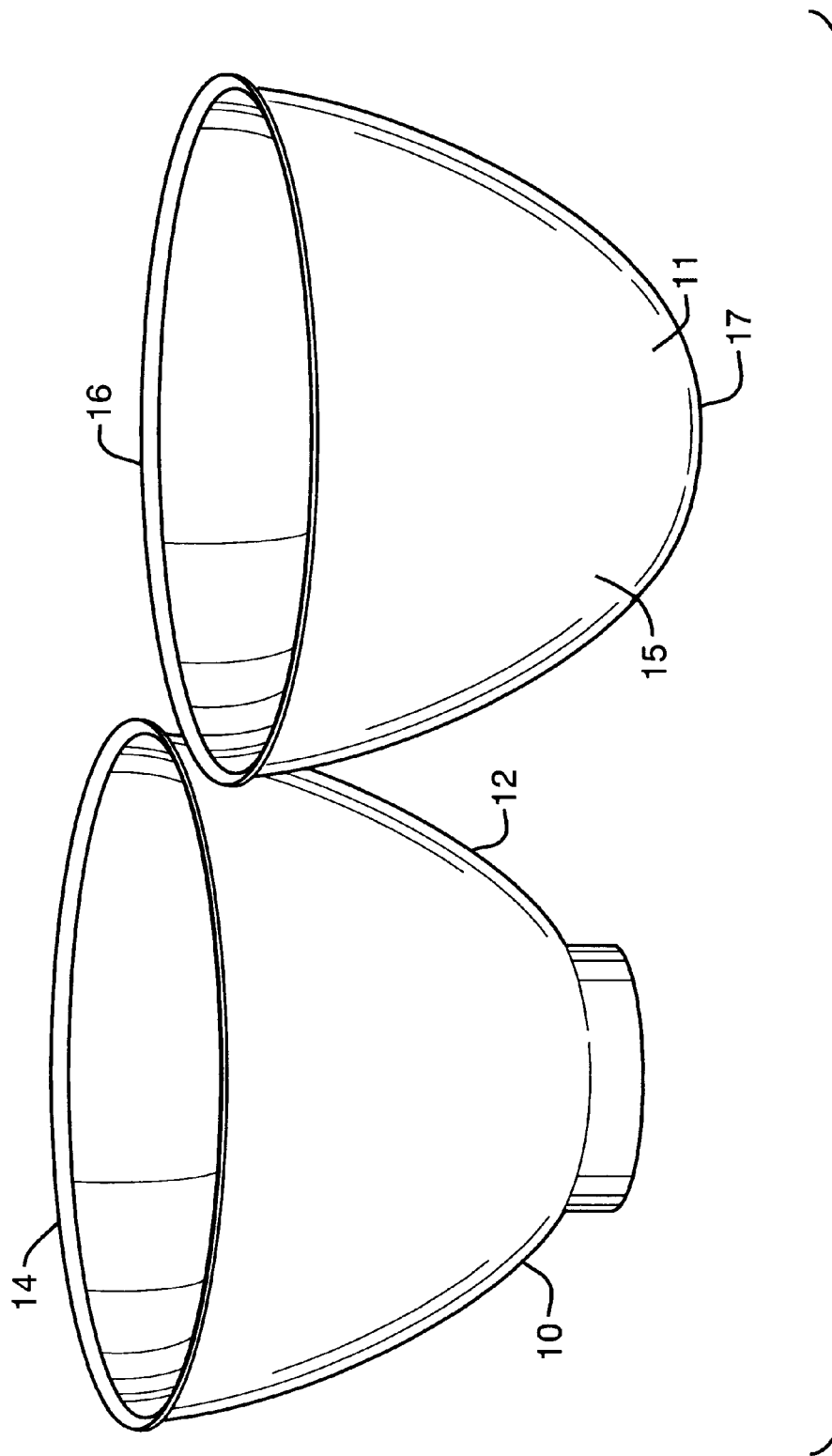

The bowl liner 11 as shown particularly in FIG. 2 includes a thin, plastic bowl-shaped body 15 that conforms to the interior of the bowl-shaped body 12 of the rubber bowl support 10. An open top 16 terminates in a bead 17 that provides a smooth edge of the bowl liner 11, but no rigidity. A base 17 is rounded so the bowl liner 11 is not free standing. Consequently, the bowl liner 11 depends entirely on the rubber bowl support 10 for strength and rigidity.

As previously indicated, prior to using this arrangement personnel within an office should rinse and dry the bowl support 10. Then they insert a new liner 11. As these are smooth bowls, it is apparent there is no ready place for an individual to grasp the bowl itself sometimes making the mixing procedure difficult as when the mixture becomes very stiff. When the materials have been mixed and used, the individual disposes of the liner 11, but the rubber bowl support 10 must also be disinfected requiring significant personnel time and facility expense to avoid cross contamination. This time and expense adds to overhead costs of a facility. Even with a disposable liner, the cleaning operations associated with reusable bowl supports and spatulas also flush debris down drains eventually clogging the drains and requiring the added overhead associated with clearing such clogged drains.

Figure 3:
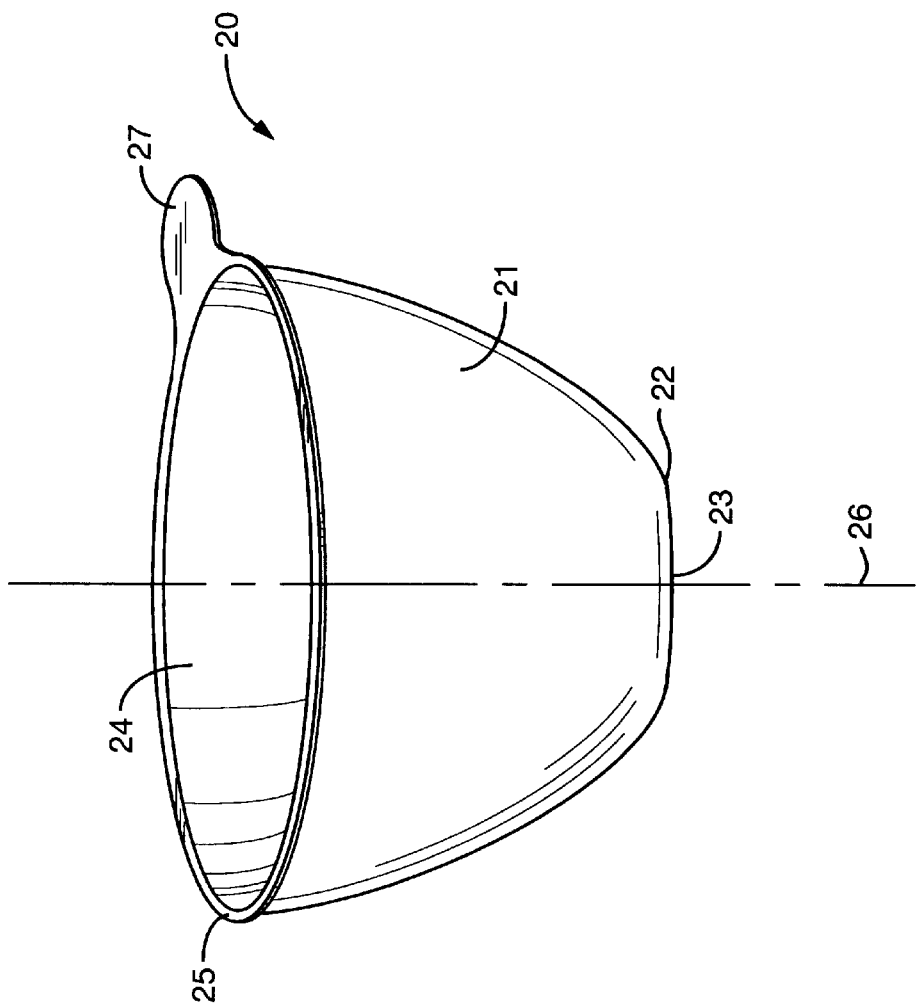
FIG. 3 is a perspective view of a free standing, disposable bowl constructed in accordance with this invention.
Figure 4:
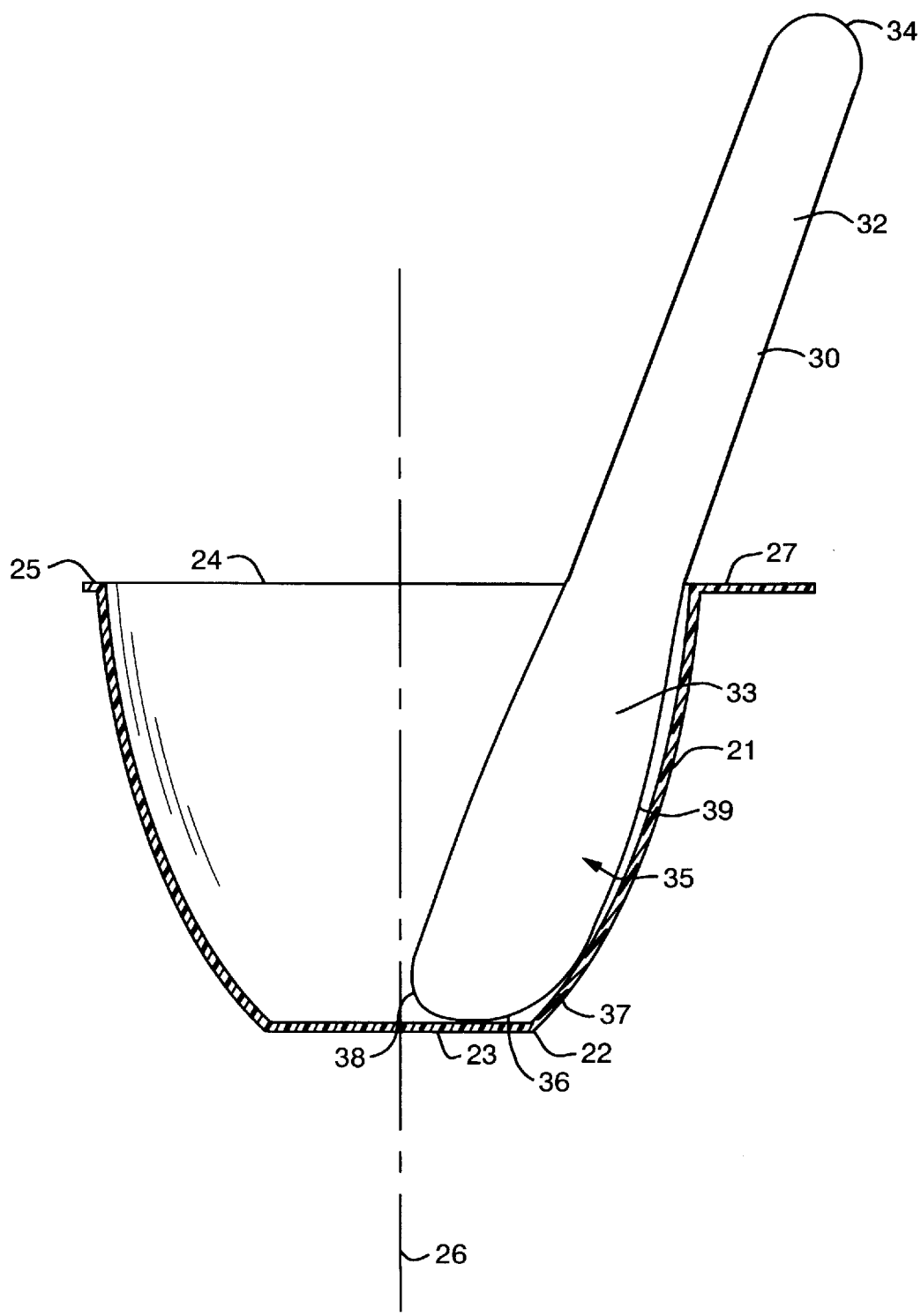
FIG. 4 is a view in partial cross-section of a bowl and spatula constructed in accordance with this invention.

FIGS. 3 and 4 depict a free-standing, disposable bowl 20 constructed in accordance with this invention. The bowl 20 has a bowl-shaped body 21 that is integrally molded from any high impact polystyrene approved as an aseptic material by the Food and Drug Administration (FDA). Such materials are well known in the art. The bowl-shaped body 21 terminates in a closed molded bottom portion 22 that defines a bottom support for the bowl. As will be apparent, the interior surface of the bottom support contacts the contents of the bowl 20 while the exterior surface contacts a supporting surface. In a preferred embodiment the bottom portion 22 is a flat surface 23. The flat surface 23 also provides a maximum transfer of energy from a vibrator to the mixture. Alternate bottom structures could be substituted for the flat surface 23.

An open top 24 carries an integrally molded lip 25 continuously and circumferentially around the open top 24 in a plane transverse to an axis 26 through the bowl 21. The lip 25 in this embodiment extends radially outwardly with respect to the axis 26. The lip 25 imparts rigidity to the entire bowl 21 so that it can act as a mixing bowl without the ancillary bowl support shown in FIGS. 1 and 2. It has been found that a lip extension of about ¼ inch provides sufficient rigidity during the mixing process for a wall thickness of 0.025".

FIGS. 3 and 4 also depict a radially extending tab 27 that facilitates handling during use. An individual can grasp the bowl about the exterior surface of the bowl portion 21 under the tab 27 and then grasp the tab 27 with the thumb thereby to firmly hold the bowl 20 in position.

As the bowl 20 requires no other external support, the bowl 20 is fully disposable and thereby inherently eliminates contamination problems. Eliminating any bowl support that is typically formed of a rubber material, also prevents latex allergic reactions by individuals using the bowl support and patients who are in close proximity to the bowl support. Consequently the mixing bowl 20 shown in FIGS. 3 and 4 is a free-standing disposable bowl that can be used for mixing materials such as alginate and gypsum mixtures, without the need for additional holders or other support paraphernalia. As will now be appreciated, the mixing bowl 20 is easy to use and inexpensive to produce.

Figure 5:
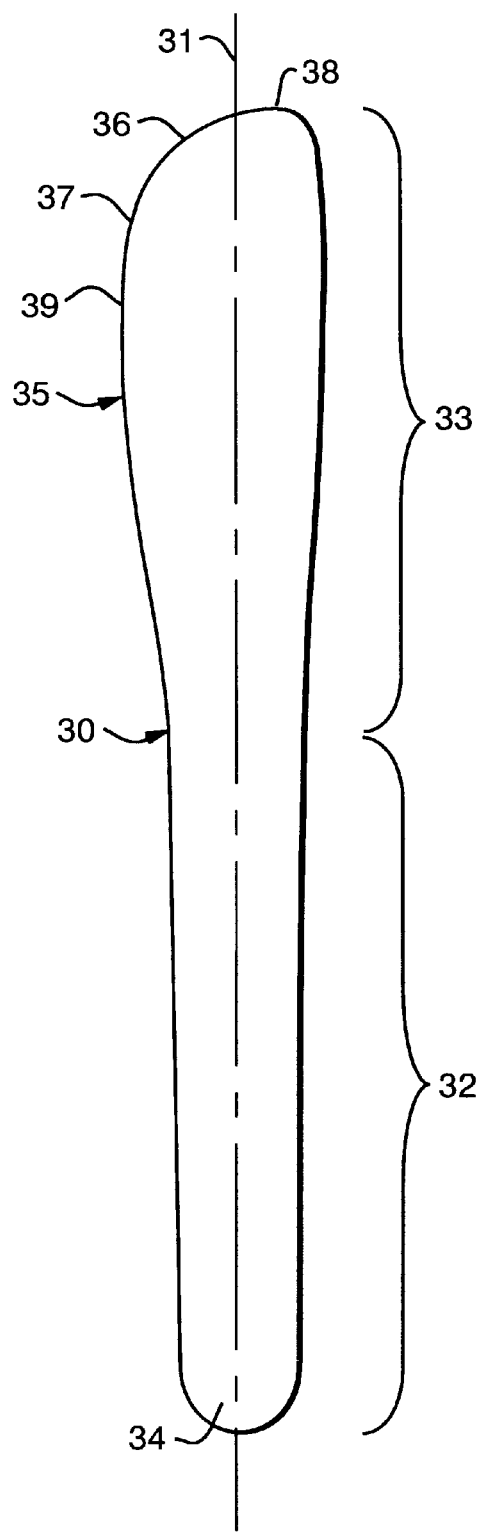
FIGS. 5 and 6 are detailed views of two different spatula embodiments.

FIGS. 4 and 5 depict a dual purpose, disposable spatula 30 that is constructed in accordance with another aspect of this invention and that can be used effectively with the mixing bowl 20. The spatula 30 extends along an axis 31, as particularly shown in FIG. 5, and is divided into two substantially equal length axial sections 32 and 33. In one embodiment the spatula is formed as a stamped, polished hardwood element that has a thickness of about ¹⁄₁₀ inch. A typical hardwood is white birch. The spatula 30 could also be injection molded from an FDA approved plastic material.

The section 32 has a substantially uniform width that is narrower than the section 33 and terminates in a constant radiused end 34. This uniform width configuration is optimized for one purpose; namely, mixing gypsum. The narrow section 32 also facilitates the use of the spatula during the placement of a gypsum mixture in a patient's impression.

The second section 33 widens from the width of the section 32 to a maximum width at 35 and then tapers back to a reduced width at the end. Both the widening and the tapering are non-symmetrical with respect to the axis 31. The second section 33 terminates in an oblique edge 36 and has radiused corners 37 and 38. The edge 36 and edge 39 are angled and shaped to conform to the structure of the base 23 and the interior shape of the bowl 20 in a vertical plane. As seen most clearly in FIG. 4, the shape of the spatula 30 readily conforms to the side and bottom of the bowl and this, together with the non-uniform width, optimizes the spatula for another purpose namely, mixing alginate.

Figure 6:
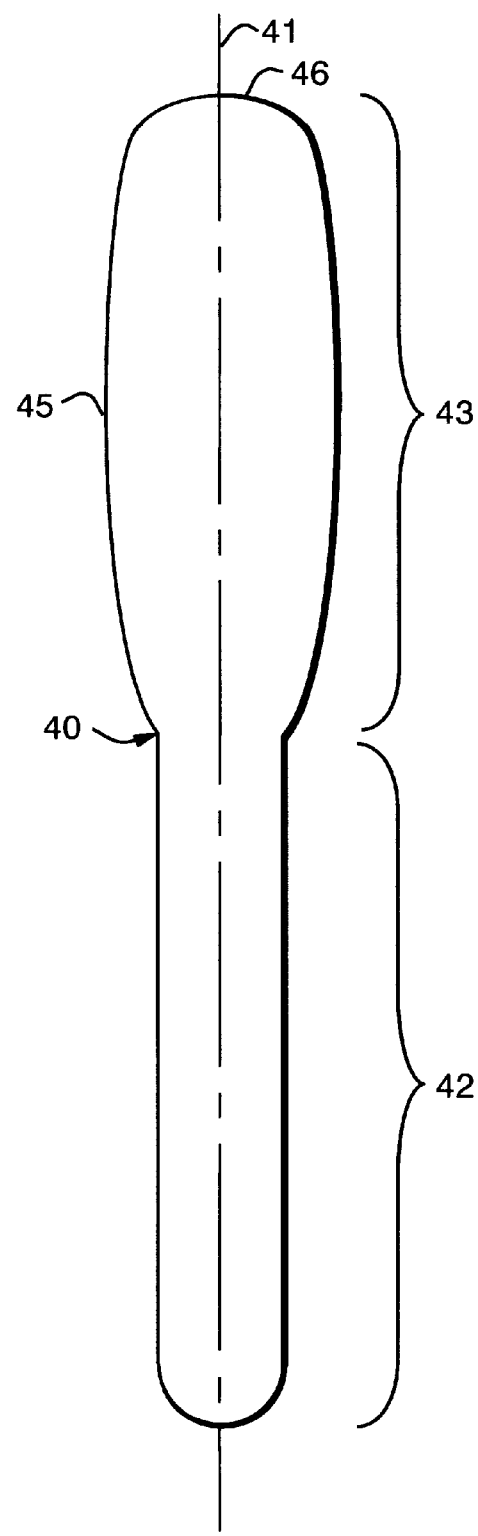

FIG. 6 depicts another embodiment of a spatula 40 that extends along an axis 41 with a first section 42 of uniform width for mixing gypsum. The second section 43 has a wider section reaching a maximum width at 45 and is symmetrical about the axis 41. The edge along the second section conforms to the side of the bowl. In this embodiment the end terminates in a single constant radius 46. The spatula 40, that can also be formed of stamped hard wood or injected molded plastic provides an alternative that will be characterized by greater flexibility at the end 46. Greater flexibility may allow an individual to apply a greater force to the spatula without its breaking.

Figure 7:
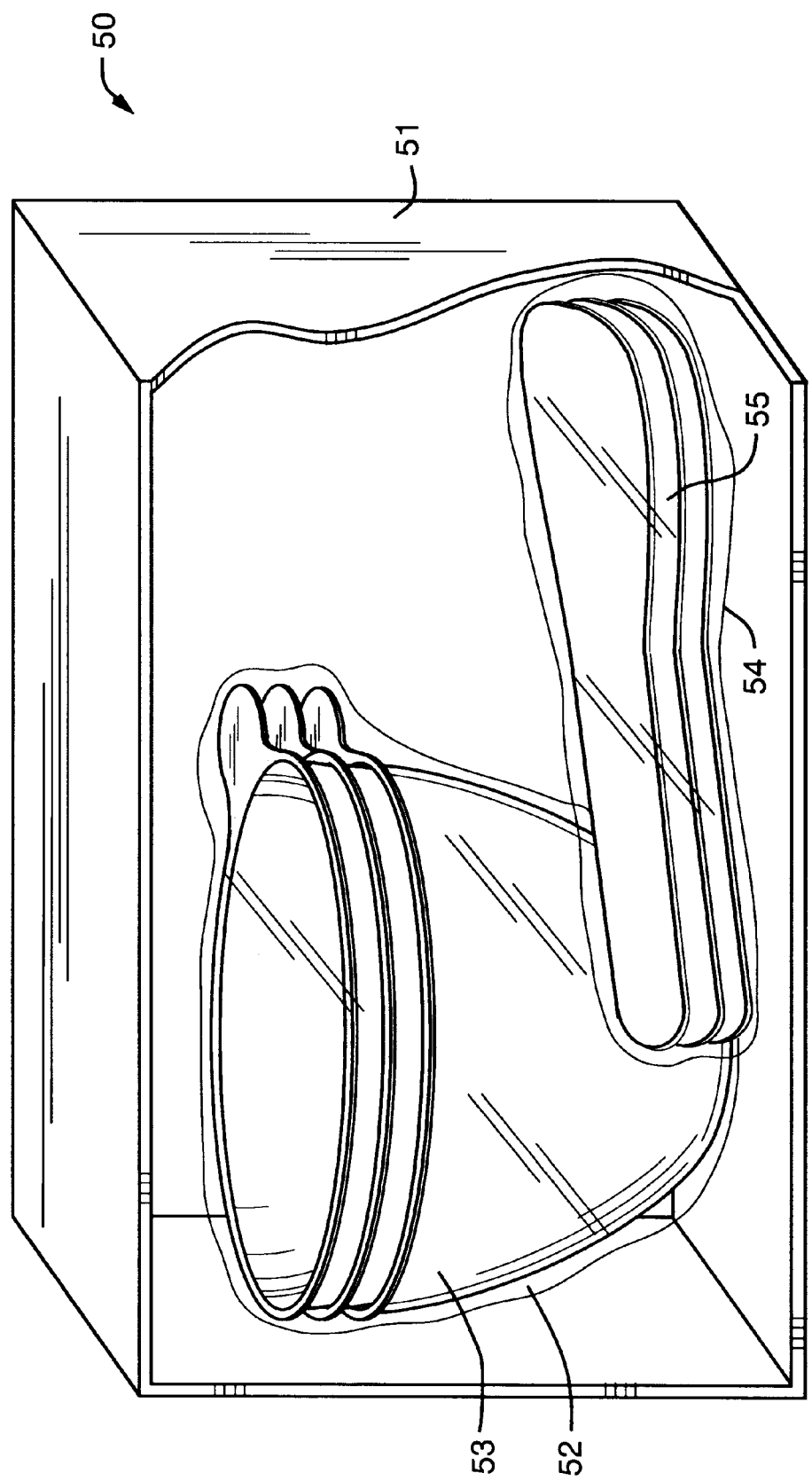
FIG. 7 is a perspective view of a kit including bowls and spatulas constructed in accordance with this invention.

FIG. 7 depicts, schematically, a kit 50 constructed in accordance with another aspect of this invention. The kit 50 includes an outer container 51 for receiving a heat sealable polyethylene storage bag 52 containing a plurality of nested bowls 53, each having the shape of the mixing bowl of FIGS. 3 and 4. The exact plurality can obviously vary; three bowls are shown being nested in this specific embodiment. A second heat sealable polyethylene package 54 carries a plurality of spatulas 55, constructed, for example, as the spatula shown in FIGS. 4 and 5 or FIG. 6. The heat sealed polyethylene packages are used to preserve cleanliness during transport and handling prior to utilization. Given the dual purpose of each spatula, the plurality of spatulas and the plurality of nested bowls 53 can be equal because one does not prepare two different mixtures in the same bowl. The outer container 51 can be further closed in a conventional manner by a sealed cover or top.

As will now be apparent, an individual uses the integral tabs to facilitate the removal of the bowl from the stack.

Figure 8:
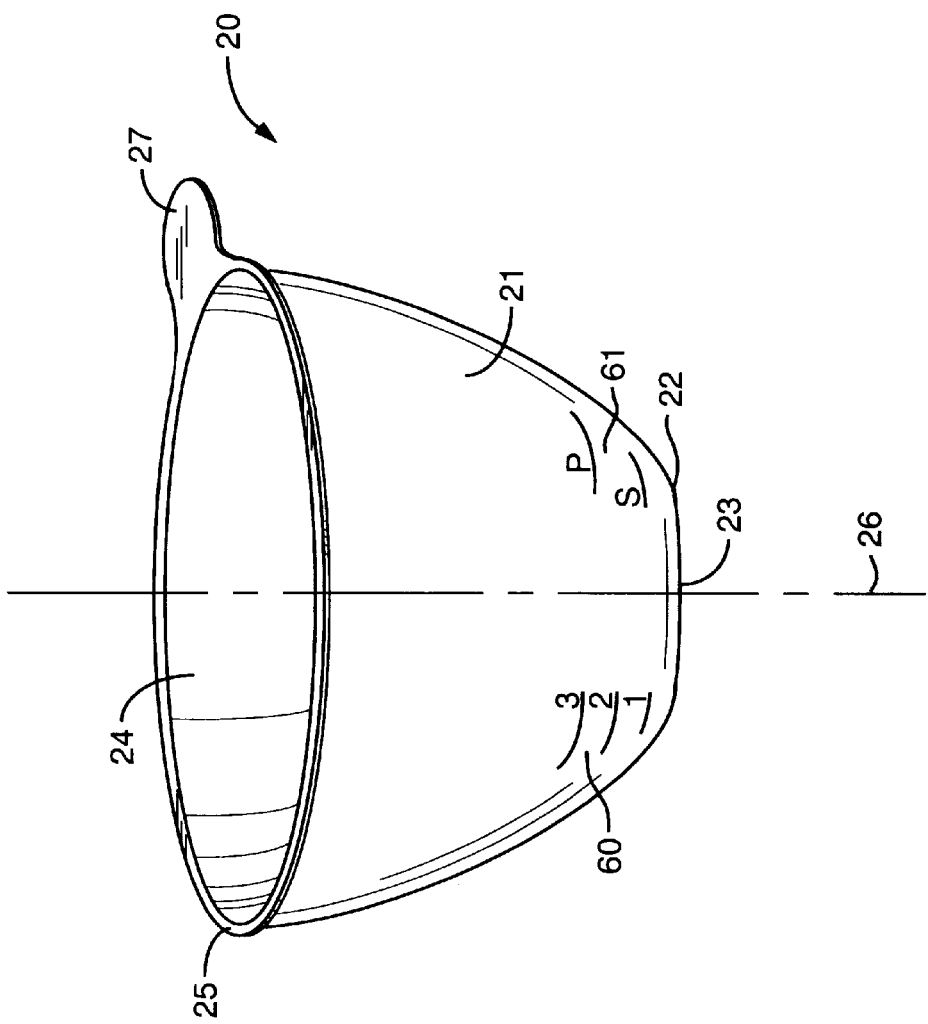
FIG. 8 is a perspective view of another embodiment of a bowl constructed in accordance with this invention.

FIG. 8 depicts another embodiment of this invention in which like reference numerals refer to like elements throughout. More specifically, FIG. 8 depicts the disposable bowl 20 with its bowl shaped body 21 and molded bottom portion 22 with a flat surface 23. The open top 24 carries the integrally molded lip 25 that extends radially outward with respect to the axis 26 to impart rigidity to the entire bowl 20. The bowl 20 also includes the radially extending tab 27 that facilitates handling during use.

This embodiment has been improved to allow the mixing of dental materials, such as alginate, stone and plaster, without the need for a separate water measuring device.

For mixing alginate a dentist will normally require 1, 2 or 3 measures of alginate. The typical measurement or given quantity is a standard scoop. The lines in the set 60 constitute visually perceptible indicia for defining a predetermined liquid volume in the mixing bowl 20 for different quantities of alginate powder. That is, the lines in the set 60 designate the water levels for 1, 2, 3 scoops of alginate material respectively.

The mixing bowl 20 in FIG. 8 also includes visually perceptible indicia for other dental materials including stone and plaster dental materials. As known, the process for mixing either stone or plaster involves a given quantity of one cup (8 oz) of stone or plaster powder. The line "S" in the set 61 of lines designates the level of water required for one cup of stone powder; the line "P", for one cup of plaster powder.

The marks may be formed by making impressions in the material or by applying a permanent mark or by printing or other means. In a preferred embodiment the indicia including their respective references and lines are integrally molded with the cup 20.

These measurement lines completely eliminate the need for a water measuring device. The mixing bowl 20 is merely placed under a faucet and filled to the appropriate line for the particular application. Problems involving contamination of separate water measuring devices are thereby eliminated.

Therefore there has been disclosed in accordance with the embodiments of this invention a system of components useful in mixing constituent ingredients, particularly in a medical facility. The components include a free-standing, disposable bowl and a dual-purpose spatula. Each free-standing, disposable bowl includes an integrally molded bowl body having a closed bottom with a planar support and an open top with an outwardly extending planar lip that imparts rigidity to the bowl. The rigidity and ease of holding the bowl, particularly when a tab is added, provide a bowl in which ingredients can be mixed without the requirement for any bowl supporting structure. Consequently the system provides a fully disposable mixing system that eliminates any need for disinfecting or other cleaning processes before or after mixing ingredients for a particular patient. As previously indicated, complete disposability leads to a number of advantages. Most importantly, disposability of the entire mixing apparatus including the mixing bowl and spatula significantly reduce the chances of cross contamination and eliminates the overhead associated with disinfecting components of prior art systems. As the mixing bowl and spatula can be constructed by conventional mass production means, direct costs for achieving complete disposability are reduced. Eliminating the disinfecting process and using the dual purpose spatulas for optimal mixing act to reduce the hand-wrist motions that can aggravate carpal tunnel syndrome, tendinitis and like medical problems. Further, complete disposability can reduce or eliminate drain clogs that can result after successive disinfecting procedures required by prior art devices wash debris down the drain. The mixing bowl of this invention is easy to use because its shape together with the radial tab facilitates an individual's grasp on the bowl during mixing. The combination of the mixing bowl and a dual-purpose spatula enable an individual to mix different ingredients in an optimal manner, further increasing efficiency.

This invention has been disclosed with reference to a particularly shaped bowl, particular thicknesses and materials. It will be apparent to those of ordinary skill in the art that various modifications to the thicknesses, materials and shapes can be made while still attaining some or all of the advantages of this invention. Therefore, it is the intent of the appended claims to cover all such variations and modifications as come within the true spirit and scope of this invention.

What is claimed as new and desired to be secured by Letters Patent of the United States is:

1. A free-standing, integrally molded plastic disposable bowl for mixing ingredients comprising:
   A) an open top bowl shaped body portion,
   B) an integral planar bottom with interior and exterior planar surfaces that is smaller than said open top and that supports said bowl on said exterior planar surface and forms the bottom interior of the bowl with said interior planar surface,
   C) an integrally formed, outwardly extending lip about the periphery of said open top for imparting rigidity to said bowl, and
   D) visually perceptible indicia means including at least one line segment and juxtaposed reference for defining a predetermined liquid volume for a given quantity of a dental material taken from the group consisting of stone, plaster and alginate dental materials.

2. A mixing bowl as recited in claim 1 wherein said visually perceptible indicia means includes a plurality of said indicia.

3. A mixing bowl as recited in claim 2 wherein each of said indicia is molded into said mixing bowl.

4. A mixing bowl as recited in claim 1 wherein said outwardly extending lip is a continuous radially, outwardly extending lip integrally molded with said bowl at said open top with a radial, coplanar tab extending from a portion of said lip.

5. A mixing bowl as recited in claim 4 wherein each of said indicia is molded into said mixing bowl and said plastic material is taken from the group consisting of FDA approved high impact polystyrene material.

6. A mixing bowl as recited in claim 1 wherein each of said indicia is molded into said mixing bowl and said plastic material is taken from the group consisting of FDA approved high impact polystyrene material.

7. A system for facilitating the mixing of ingredients in a dental facility including:
   A) a free-standing, integrally molded, plastic disposable bowl including:
      i) an open top bowl shaped body portion,
      ii) a planar bottom portion with interior and exterior planar surfaces that is smaller than said open top and that supports said bowl on said exterior planar surface and forms the bottom of the bowl with said interior planar surface,
      iii) an outwardly extending lip at said open top for imparting rigidity to said bowl, and
      iv) visually perceptible indicia means including at least one line segment for defining at least one predetermined liquid volume for a given volume of a dental material taken from the group comprising stone, plaster and alginate dental materials, and
   B) a disposable spatula for mixing the ingredients in the disposable bowl.

8. A mixing system as recited in claim 7 wherein said visually perceptible indicia include a plurality of said indicia.

9. A mixing system as recited in claim 8 wherein each of said indicia is molded into said mixing bowl.

10. A mixing system as recited in claim 7 wherein said bowl has a predetermined contour adjacent the bottom thereof and said spatula comprises an elongated, uniformly thin structure defining first and second axial sections wherein said first section has a uniform width and terminates in a radiused end and wherein said second section has a non-uniform width with an edge contoured to conform to the contour of said bowl.

11. A mixing system as recited in claim 10 wherein each of said indicia is molded into said mixing bowl.

12. A mixing system as recited in claim 7 wherein said lip extends radially outwardly from said bowl and has an integrally molded, radial, coplanar tab extending from a portion of said lip.

13. A mixing system as recited in claim 12 wherein each of said indicia is molded into said mixing bowl.

14. A kit for enabling the mixing of materials in a dental facility comprising:
   A) a first plurality of nested, free-standing, disposable bowls for mixing ingredients, each said disposable bowl comprising a plastic bowl shaped portion having a closed planar bottom and open top and being integrally molded from an FDA approved high impact polystyrene material, said closed bottom being smaller than said open top and being flat with interior and exterior planar surfaces whereby said exterior planar surface provides a planar support for said bowl in an upstanding orientation and said interior planar surface contacts contents of the bowl, said bowl additionally including an integrally molded, radially outwardly extending, continuous circumferential planar lip about said open top for imparting rigidity to said bowl and visually perceptible indicia means molded in said bowl to define at least one indicia including a line segment and juxtaposed reference for defining a predetermined liquid volume for a given quantity of a dental material taken from the group consisting of stone, plaster and alginate dental materials,
   B) a second plurality of disposable spatulas for mixing the ingredients in the disposable bowls, and
   C) packaging containing said pluralities of bowls and spatulas.

15. A kit as recited in claim 14 wherein said first and second pluralities are equal.

16. A kit as recited in claim 14 wherein each said spatula comprises an elongated, uniformly thin structure defining first and second axial sections, said first section having a uniform width that terminates in a radiused end and said second section having a non-uniform width with an edge contoured to conform to the contour of said bowl.

17. A kit as recited in claim 14 wherein said visually perceptible indicia means includes a plurality of said indicia.

18. A kit as recited in claim 17 wherein said first and second pluralities are equal.

19. A kit as recited in claim 17 wherein each said spatula comprises an elongated, uniformly thin structure defining first and second axial sections, said first section having a uniform width that terminates in a radiused end and said second section having a non-uniform width with an edge contoured to conform to the contour of said bowl.

* * * * *